(12) United States Patent
König et al.

(10) Patent No.: US 12,123,047 B2
(45) Date of Patent: Oct. 22, 2024

(54) METHODS FOR CORRELATIVE MICROSCOPY

(71) Applicant: Leica Mikrosysteme GmbH, Vienna (AT)

(72) Inventors: Julia König, Vienna (AT); Paul Wurzinger, Deutsch-Wagram (AT)

(73) Assignee: Leica Mikrosysteme GmbH, Vienna (AT)

( * ) Notice: Subject to any disclaimer, the term of this patent is extended or adjusted under 35 U.S.C. 154(b) by 337 days.

(21) Appl. No.: 17/839,586

(22) Filed: Jun. 14, 2022

(65) Prior Publication Data
US 2022/0403440 A1 Dec. 22, 2022

(30) Foreign Application Priority Data

Jun. 17, 2021 (EP) .................................... 21180173
Sep. 6, 2021 (EP) .................................... 21195045

(51) Int. Cl.
*C12Q 1/02* (2006.01)
*G01N 1/28* (2006.01)
(Continued)

(52) U.S. Cl.
CPC .............. *C12Q 1/02* (2013.01); *G01N 1/286* (2013.01); *G01N 1/42* (2013.01); *G01N 21/6458* (2013.01);
(Continued)

(58) Field of Classification Search
CPC . C12Q 1/02; G01N 1/286; G01N 1/42; G01N 21/6458; G01N 23/04; G01N 23/06;
(Continued)

(56) References Cited

U.S. PATENT DOCUMENTS 5,841,892 A * 11/1998 McGrath .................. G06T 7/73
382/173
2010/0093023 A1* 4/2010 Gustafsson ............ G01N 1/286
435/40.52
(Continued)

FOREIGN PATENT DOCUMENTS

WO 2016/016000 A1 2/2016

OTHER PUBLICATIONS

Gibson, Kimberley H. et al., Fluorescing the Electron: Strategies in Correlative Experimental Design, Chapter 2 in: Müller-Reichert, T. and Verkade, P. (eds.), Correlative Light and Electron Microscopy II, Methods in Cell Biology, vol. 124, pp. 23-54, Elsevier/Academic Press 2014.
(Continued)

*Primary Examiner* — Nicole M Ippolito
(74) *Attorney, Agent, or Firm* — Hodgson Russ LLP (57) ABSTRACT

A method (400) for microscopic examination of a sample (1) includes applying (410) the sample (1) to a sample holder (10) having a transparent carrier material, capturing (420) a first image (210, 220) of the sample (1) applied to the sample holder (10) using a first light-microscopy method, cryofixing, freeze-substituting, and subsequently infiltrating and embedding (430) the sample (1) together with the sample holder (10) with an embedding medium (20) in an embedding mold (90, 100), curing (440) the embedding medium (20), removing the sample (1) from the embedding mold (90, 100) together with the embedding medium (20) and the sample holder (10), capturing (450) a second image (230) of the sample (1) embedded in the cured embedding medium (20) using a second light-microscopy method, wherein at least partially identical regions of the sample (1) are captured in the first and second images, and identifying (460) at least one portion of the first image (210, 220) and one
(Continued)

portion of the second image (230) which show identical regions of the sample (1).

18 Claims, 7 Drawing Sheets

(51) Int. Cl.
    *G01N 1/42*     (2006.01)
    *G01N 21/64*     (2006.01)
    *G01N 23/04*     (2018.01)
    *G01N 23/06*     (2018.01)

(52) U.S. Cl.
    CPC .............. *G01N 23/04* (2013.01); *G01N 23/06* (2013.01); *G01N 2001/2873* (2013.01); *G01N 2223/04* (2013.01); *G01N 2223/418* (2013.01)

(58) Field of Classification Search
    CPC ....... G01N 2001/2873; G01N 2223/04; G01N 2223/418
    See application file for complete search history.

(56) References Cited

U.S. PATENT DOCUMENTS

| | | | |
|---|---|---|---|
| 2012/0027650 A1* | 2/2012 | Goodman | G02B 21/26 250/307 |
| 2016/0252719 A1 | 9/2016 | Liu et al. | |
| 2017/0067800 A1* | 3/2017 | Briggman | H01J 37/26 |

OTHER PUBLICATIONS

De Boer, Pascal et al., Correlated light and electron microscopy: ultrastructure lights up!, Nature Methods, vol. 12, No. 6, Jun. 2015, pp. 503-513, New York.
Bykov, Yury S. et al., Correlative light and electron microscopy methods for the study of virus-cell interactions, FEBS Letters, vol. 590, pp. 1877-1895, Apr. 13, 2016, Federation of European Biochemical Societies, Amsterdam, the Netherlands.
Ando, Toshio et al., The 2018 correlative microscopy techniques roadmap, Journal of Physics D: Applied Physics, vol. 51, No. 44, 443001, Aug. 31, 2018, IOP Publishing Ltd, the United Kingdom.

* cited by examiner

METHODS FOR CORRELATIVE MICROSCOPY

CROSS-REFERENCE TO RELATED APPLICATIONS

The present application claims the benefit of and priority to European Patent Application No. 21180173.3, filed Jun. 17, 2021, and European Patent Application No. 21195045.6, filed Sep. 6, 2021, the entire disclosures of which are incorporated herein by reference.

FIELD OF THE DISCLOSURE

The present disclosure relates to the fields of light microscopy and correlative microscopy.

The disclosure relates to a method for assigning regions of a biological sample imaged in light-microscopy captures to the same sample regions after high-pressure freezing and freeze substitution as well as cryosubstitution and embedding in an embedding medium.

BACKGROUND

Correlative light and electron microscopy (CLEM) is well known and is described, for example, in Gibson, K. H. et al., Fluorescing the Electron: Strategies in Correlative Experimental Design, Chapter 2 in: Müller-Reichert, T. and Verkade, P. (eds.), Correlative Light and Electron Microscopy II, Methods in Cell Biology, Vol. 124, Elsevier/Academic Press 2014. In correlative light and electron microscopy, samples are first examined using light microscopy or fluorescence microscopy, then prepared for electron microscopy, and finally analyzed using electron microscopy, with image data obtained using light and electron microscopy being correlated with one another.

Biological samples in the form of cell colonies, cell cultures, biofilms, and the like are often grown on or cultivated on transparent materials, which thus act as carrier materials or sample holders for these samples. In correlative light and electron microscopy, preparations of these samples should first be made accessible to light-microscopy examination and then to electron-microscopy examination. In this case, certain sample regions, e.g. certain cells, cell structures, etc., are to be examined.

For this purpose, the samples applied to or cultivated on a sample holder (e.g. consisting of a transparent carrier material such as quartz) are typically first examined under a light microscope, for example by means of transmitted light microscopy. The samples located on the sample holder are then cryofixed, freeze-substituted, and simultaneously infiltrated by and embedded in an embedding medium such as synthetic resin. Said embedding medium is then cured. The sample (e.g. the cells to be examined) is constantly in contact with the sample holder. The embedding results in preparation blocks from which ultra-thin portions can be produced using an ultramicrotome.

In correlative light and electron microscopy, it is sometimes desirable to relocate regions of interest in the sample, for example certain cell aggregates or cells that display a certain physiological reaction or property, which were identified before they were fixed on the sample holder, after they have been fixed, or to compare them using light microscopy. An object of the disclosure is in particular to specify a method that advantageously makes this possible.

SUMMARY

In this context, the disclosure proposes a method with the features of the main claim. Embodiments of the disclosure can be found in the dependent claims and the following description.

Before the further explanation of the measures proposed according to the disclosure, techniques that can be used within the scope of the present disclosure will be explained and terms used to explain the disclosure will be defined.

Cryofixation is a sample preparation method frequently used in electron microscopy. An aqueous sample is cooled very quickly to a temperature below −150° C. and solidifies substantially without the formation of ice crystals. The cryofixation is carried out, for example, by means of or in the form of high-pressure freezing (see below). Cryofixation has proven to be particularly suitable for structural biology examinations. The objects to be examined, such as cells, enzymes, viruses, or lipid layers, are thus embedded in a vitrified layer of ice. The great advantage of cryofixation is that the biological structures can be preserved in their native state. Among other things, a biological process can be stopped at any point in time by cryofixation and examined in this vitrified state, e.g. in a cryo-electron microscope, but also in a light microscope with appropriate sample cooling, with cryo-light microscopy primarily being used to find relevant regions in the sample, which regions are marked and then looked at more closely in a cryo-electron microscope. A suitable light microscope for this is known, for example, from WO 2016/016000 A1.

High-pressure freezing is the freezing of samples under high pressure. It is a cryofixation process. For example, freezing at pressures of around 2000 bar suppresses the formation of ice crystals and prevents structural damage to the sample, because water changes directly from the liquid to the vitrified state at the corresponding pressures.

Freeze substitution is a procedure commonly used after high-pressure freezing and other cryofixation processes. It involves removing the water from the frozen sample using an organic solvent at low temperatures and often in the presence of a secondary fixing means. The solvent is then replaced by a curable or polymerizable material, such as a synthetic resin. Once the freeze substitution is complete, curing typically occurs through polymerization of the synthetic resin, e.g. epoxy resin.

After curing, the sample holder is detached. In the present disclosure, the term "preparation block" should be understood to mean the cured block consisting of the cured embedding medium including the embedded sample. Sample regions that showed reactions or cell states of interest under the light microscope are then further prepared for electron-microscopy examination. A goal is to be able to capture sample regions of interest, which have previously been identified using the light microscope, in a targeted manner during the electron-microscopy image capture. To support the correlation between the light-microscopy and electron-microscopy images, the sample holder is usually structured or covered/coated with a locally clearly distinguishable lattice or mesh structure.

The preparations are often embedded and cured in so-called cryotubes (also referred to as cryovials or microtubes) from various manufacturers, which are typically cylindrical in the upper region and taper conically toward the base. The sample holder with the sample in the embedding medium sinks in the cryotube so far that it is completely surrounded by the vessel and the resulting preparation block is divided into two parts. Cryotubes designed in this way often lead to the sample holder being positioned at an angle in the lower, conical region, and the sample is therefore not aligned in a defined manner. In addition, the method is largely unusable for broken sample holders because in such cryotubes the fragments are completely surrounded by the cured embedding medium (the preparation block) and are almost impossible to separate from the preparation block.

The applicant therefore proposes so-called flow-through rings or flow-through inserts (for use in a surrounding tray) in which the sample holder rests against the entire surface of a boundary structure (namely the base of a substantially cylindrical ring portion). As a result, the cured block is on the side of the carrier material covered with the sample, while only a thin polymer film forms on the back between the mold base and the carrier material. The base is adapted to the dimensions of the sample holder. This prevents a disadvantageous tilting/inclination of the sample holder. The use of corresponding rings or inserts is common in the art and is described, for example, in the aforementioned publication by Gibson et al. Corresponding vessels have, as already expressed in other words, at least one cylindrical portion, the inner diameter of which is dimensioned such that the sample holder can be inserted into it, the cylindrical portion having an inwardly projecting structure at one axial end, which is used for support of the sample holder, for example.

The interface between the cured preparation block and the sample holder often becomes damaged or uneven during sample holder detachment. The lattice or mesh structure on the carrier material, which is often applied by means of a coating and which could be used as a guide in the light-microscopy examination, often detaches (locally) with the carrier material of the sample holder, making the assignment between living and freeze-substituted and cured preparation parts difficult and imprecise. Local damage to the block surface (i.e., a surface of the block consisting of the embedding medium in which the sample was embedded, for example a synthetic resin block) leads to local gaps in the evaluation and can also seriously impair the assignment of undamaged preparation parts.

Within this context, the present disclosure achieves an easy-to-implement and cost-effective method that enables simple and fault-tolerant identification and assignment of corresponding image regions of images of the original sample and allows captures in later examination steps, such as electron-microscopy captures in the context of the aforementioned correlative light and electron microscopy.

According to a first aspect of the disclosure, a method according to the disclosure for the microscopic examination of a sample comprises the steps provided according to the main claim and explained in more detail below:

applying the sample to a sample holder comprising or consisting of a transparent carrier material, capturing a first image of the sample applied to the sample holder using a first light-microscopy procedure (in the case of examining living cells, in particular a light-microscopy procedure that is suitable for living cell microscopy), cryofixing, freeze-substituting, and subsequently infiltrating and embedding the sample with an embedding medium, for example a synthetic resin, in an embedding mold, curing, e.g. polymerizing, the embedding medium, removing the sample embedded in the cured embedding medium from the embedding mold together with the embedding medium and the sample holder, strictly optional: detaching (removing) the cured embedding medium from the back (the side of the sample holder that faces away from the sample) of the sample holder, this cleaning preferably being carried out at least partially mechanically, although it can also be supported by chemical cleaning agents such as ethanol, capturing a second image of the sample embedded in the cured embedding medium using the first or a second light-microscopy procedure, while the sample holder on the side facing the sample adheres to the cured embedding medium or at least to a part thereof that has not been removed beforehand, in particular through the sample holder, wherein the second image is represented by second image data and at least partially identical regions of the sample are captured by means of the first and second captures, and, finally, identifying at least one portion of the first image and at least one portion of the second image which show identical regions of the sample.

In the context of this application, "capturing an image" should be understood in a generalized manner and also includes the capture of, for example, image sequences such as temporal/spatial image series and focus series or combinations thereof. Examples of light-microscopy procedures that can be used as the first and/or the second light-microscopy procedure are forms of light microscopy such as transmitted light microscopy, reflected light microscopy, fluorescence microscopy, etc. and combinations thereof. Both scanning-microscopy and widefield-microscopy procedures can be used here. It is also conceivable for different partial images of an image to be captured with different forms of light microscopy; such a combined capture procedure is also a light-microscopy procedure within the scope of the application. A captured image is represented in each case by the captured image data.

As the starting material for the method according to the disclosure, samples such as cells or tissue parts are applied to a sample holder, i.e. grown and/or received, for example, and imaged with a light microscope. Since such samples are often still alive until they are cryofixed (i.e. represent a living preparation), it is particularly advantageous if the sample to be imaged is kept under controlled conditions, i.e. particularly physiologically favorable conditions or conditions that cause a specific physiological reaction, until and/or during the capturing of the first image. Physiologically favorable conditions should be understood to mean environmental conditions which are not harmful to a living sample to be examined, such as a cell or a plurality of cells, and in particular ensure undisturbed physiological reactions. For example, for this purpose the sample can be accommodated together with a sample holder in a capsule in which a certain temperature and/or composition of the air (for example a certain oxygen content) is ensured.

An image of a sample within the meaning of the present application means an at least partial picture of the sample. An image of a sample can therefore show the entire sample or only sub-regions thereof. The method according to the disclosure is therefore not limited to images of the entire sample. Within the scope of this application, the concept of an image should also include spatial or temporal sequences of individual images (image series) as long as at least one of these partial images contains a partial image of the sample (i.e. shows a sub-region of the sample).

Transmitted-light bright-field microscopy is particularly suitable as a light-microscopy procedure for capturing both the first and the second image, although, as mentioned above, a wide range of light-microscopy procedures such as reflected light microscopy, fluorescence microscopy, confocal microscopy or multiphoton microscopy is conceivable. Both scanning and camera-based procedures (widefield microscopes) are also conceivable.

Furthermore, an image of the sample can also be composed of a plurality of partial captures (single images). These partial images are then combined to form a large-area aggregate image for the further method steps (stitching).

According to a further aspect of the disclosure, the capture of the first image and the second image is preferably carried out using the same microscope or a microscope of the same type. This ensures a simple comparability between the first and second image.

According to a further aspect of the disclosure, the first image is captured and the second image is captured using the same lens and/or at the same magnification and/or using the same scan region and/or the same image resolution. Here, too, the aim is to ensure that the conditions for the image capture are as comparable as possible, in order to ensure good comparability of the first and the second image. In particular, it is also advantageous for the first image and the second image to be captured from the same side of the sample, i.e. through the transparent carrier material or the sample holder, for example. This also results in an advantage of the aforementioned use of the same lens, since this lens is advantageously corrected for the imaging through the sample holder used.

After the steps described above have been carried out, and before the further processing of the cured preparation, the sample holder is typically at least partially detached from the preparation (i.e. the sample embedded in the embedding medium) after capturing the second image.

According to the disclosure, the samples applied to a sample holder are preferably examined through the carrier material (the material of the sample holder) at least for the capturing of the second image. The second image is thus preferably captured through the sample holder. For this purpose, the sample is typically illuminated and also imaged from the side of the sample holder facing away from the sample (the back) through a single lens. The carrier material must therefore be an at least partially transparent material, e.g. glass or sapphire. For example, a cover glass or a sapphire plate polished to optical quality is suitable for a sample holder. In a preferred version of the method according to the disclosure, a glass or sapphire is consequently used as the carrier material.

In order to ensure that the image is of high quality, it is advantageous to remove the embedding medium from the side facing away from the sample (the back) when the second image is captured through the sample holder in order to ensure good optical quality of the image. Sapphire is particularly advantageous here because it can be mechanically separated from the embedding medium relatively easily due to its hardness: if sapphire is used, metal and soft abrasive materials can be used to remove the embedding medium from the sample holder without scratching the surface of the sample holder. The embedding medium can thus be removed completely or at least as far as possible, so that the surface of the sample holder regains sufficient optical quality and allows the best possible imaging or capturing of the second image.

According to the disclosure, a synthetic resin, in particular an epoxy resin, is preferably used as the embedding medium.

A final detachment of the sample holder from the preparation block for the purpose of further processing can be done, for example, by immersion in LN$_2$ (liquid nitrogen), the different thermal expansion coefficients of embedding medium and sample holder leading to the sample holder coming off. Alternatively or additionally, it is also possible to detach the sample holder with a blade such as a scalpel blade.

A particularly preferred variant of the method according to the disclosure uses an embedding medium which has autofluorescence, i.e. is capable of autofluorescence, for example a synthetic resin. This autofluorescence is used to carry out the second light-microscopy capture: the embedding medium can be excited to autofluorescence, for example by means of an external light source such as an LED or a laser, for the purpose of image capture. The fluorescent light then in turn irradiates the sample and thus serves as a transmitted light source for capturing the second light-microscopy image. The second light-microscopy image is thus captured by transmitted-light bright-field microscopy. This makes it possible in a particularly simple manner to make a microscopic capture of the preparation without having to prepare it in a special way.

A smooth surface of the preparation block at the entry point of the light is advantageous for entry with as little loss as possible, but not essential. Another advantage of this variant is that (in contrast to direct transmitted light illumination of the sample) a certain absorption of the incident light is acceptable due to the light generated for transmitted light illumination near the sample: the method can be carried out despite the lack of transparency of the embedding medium for the wavelength of the light from the external light source and/or the wavelength of the autofluorescence. Furthermore, in this variant, the preparation block can be illuminated from any direction, for example illumination and detection can be carried out through opposite sides of the preparation block or the direction of the illumination can be perpendicular to the direction of detection. Simultaneous or time-delayed illumination from several directions is of course also conceivable, for example by means of a plurality of artificial light sources, for example several LEDs and/or lasers, or a plurality of partial beams that are generated by splitting the light from a single light source. Perpendicular incidence of the light on a surface of the preparation block is often preferable in order to prevent reflections, although other directions of incidence are also conceivable.

It is particularly advantageous for this method if the illumination by means of an artificial light source is carried out through the same lens of a microscope that is also used for imaging the sample, i.e. in the second light-microscopy procedure. In other words, the microscope is used for both illumination and detection, and illumination and detection are carried out through the same lens.

A more complex alternative to achieve particularly good transmitted light illumination (without or in addition to using autofluorescence of the embedding medium) is to cut off the preparation block (cured block including the sample) and then polish (smooth) it so that the surface is as smooth as possible and a low-loss (i.e. as reflection- and scatter-free as possible) entry of light from an external light source into the preparation block is made possible. If such a polishing does not take place, the illumination is dependent on the fact that good (i.e. with little loss) illumination may also occur at the point of interest, which is typically not the case due to the meniscus formation of the synthetic resin on the walls of the polymerization mold. In this case, too, the detection is again preferably carried out through the sample holder. Such a polishing of the entry point is of course also advantageous if the autofluorescence of the embedding medium is used, in order to minimize the losses when the light enters the preparation block and thus to maximize the autofluorescence.

As an alternative or in addition to using any autofluorescence of the embedding medium that may be present, it is also possible for a sample that is capable of fluorescence to be used and for the second light-microscopy procedure to detect the fluorescence of the sample. In this case, the second light-microscopy procedure is consequently a fluorescence microscopic procedure. Here, too, the illumination (excitation) of the sample and the detection of the fluorescent light can be carried out through the same lens of a microscope. If the illumination does not take place through the sample holder, polishing the entry point of the light as described above is also advantageous in the case of excitation of a fluorescence of the sample.

In order to ensure simple further processing and good illumination or detection through the sample holder, the method according to the disclosure is preferably carried out using a suitable cryotube with a sufficiently wide, planar base: The sample holder with the sample is thus preferably placed in a cryotube with a flat base, wherein the maximum extension of the base is greater than or equal to the maximum extension of the sample holder. The embedding medium is then fed into the cryotube with the sample at least until the sample is completely surrounded by the embedding medium, wherein the sample holder is oriented so as to be parallel or substantially parallel to the base of the cryotube even after the feeding of the embedding medium. Suitable cryotubes for such a method are, for example, the aforementioned flow-through rings/inserts.

According to a further aspect of the disclosure, corresponding sample regions are identified on the basis of the first image data and the second image data using a first algorithm, for example using image-recognition methods. Such an algorithm can at least partially use machine-based methods (machine learning/deep learning) in order to identify similar structures in both images or the corresponding image data. Corresponding sample regions are typically identified by analyzing the sample structure itself, but can also be supported by an artificial lattice or mesh structure applied (for example by coating) to the sample holder. Alternatively or additionally, it is of course also conceivable for corresponding image regions/structures in the images not to be identified automatically by an algorithm, but manually (i.e. by a user of appropriate image processing software).

Preferably, a first coordinate system is assigned to the first image and a second coordinate system is assigned to the second image and, based on the image regions identified with one another, a coordinate transformation between the first coordinate system and the second coordinate system is determined by the first algorithm or by a separate second algorithm. In this regard, it should be emphasized that the use of an algorithm (i.e. a software) to determine a coordinate transformation is independent of whether an algorithm has already been used to identify corresponding sample regions. The coordinate transformation can be determined in portions for local regions (region-related), such as for specific sample structures, or continuously for the entire preparation, depending on the task. Different coordinate transformations can thus be defined for different sample regions and/or different cell types within the sample. A coordinate transformation determined only for selected local regions is advantageous, for example, when certain parts of the sample (such as individual cells) have shifted (delocalized) after the first image was captured and before the second image was captured. In this case, it is advantageous to determine the coordinate transformation only on the basis of the parts of the sample whose position has not changed (e.g. fixed cells). An experienced user and accordingly also a correspondingly trained neural network is able to identify delocalized sub-regions, for example by means of exclusion methods, and to select only non-delocalized sub-regions for determining the coordinate transformation. Once a coordinate transformation has been determined, those sub-regions of the sample that have been delocalized can be easily determined in the first image, since these are all where the coordinate transformation cannot find a corresponding counterpart in the second image. Again, these delocalized regions can typically still be identified in the second image by means of exclusion methods or the like.

The second coordinate system and the coordinate transformation that assigns the first image to the second image (or vice versa) can be used with the image data of the second image for further (subsequent) evaluation and/or processing steps according to a further aspect of the disclosure. A direct relationship to data from the first image can thus be established in subsequent processing steps.

In a particularly advantageous embodiment of the method according to the disclosure, a continuous coordinate system is assigned to the cured preparation block and transformation specifications (coordinate transformations) are determined which geometrically map corresponding image portions of the original sample onto the embedded sample. The coordinate and transformation specifications defined in this way can also be adopted in further preparation steps. For example, image data from the first light-microscopy procedure (i.e. the original sample/the living preparation) can be assigned directly to a point in a finished TEM preparation of the sample by means of transformation.

The method according to the disclosure can therefore in particular also be part of a larger sample processing and image capturing process, in particular a method for carrying out correlative light and electron microscopy (CLEM). This would be followed by a cutting process (for example using a microtome, preferably an ultramicrotome) and an examination using an electron microscope (for example a transmission electron microscope (TEM)) after the preparation block has been at least partially detached from the sample holder. After at least partial detachment of the cured embedding medium with the cured sample from the sample holder, sample portions can be made by cutting the sample in the embedding medium embedding the sample (i.e. by cutting the preparation block), with these sample portions then being examined in an electron microscope. The transformation specifications obtained within the scope of the method according to the disclosure, including the defined coordinate systems, can be transmitted to the devices used subsequently (such as an electron microscope) and processed there and/or taken into account when carrying out further process steps.

In summary, an important aspect of the disclosure is to capture a second light-microscopy image of the embedded sample while it is still in firm contact with the sample holder used, and to advantageously also carry out this capturing in such a way that the resolution of the second image is as similar as possible to that of the first image, specifically by imaging all or at least a large part of the preparation. This second image should then be oriented toward the first image by the user or by an electronic correlation routine, and the image regions should be assigned. Alternatively, an inverse transformation is of course also possible: the first image can also be reoriented and the image regions assigned to the regions of the second image. The second image is captured in particular through the sample holder.

This procedure makes it possible to achieve an exact assignment between sample regions in the preparation block or the second image and the same sample regions in the original sample or the first image. If the block surface is damaged due to the detachment of the carrier material, or if the lattice or mesh structure is lost in whole or in part, the scans of the undamaged block provide the best possible data for the relocation of individual sample regions of interest. This relocalization can be carried out by looking for coordinate points or by local correlation of the scan with undamaged sample regions. It also opens up the possibility of automated further processing.

The method according to the disclosure achieves a significantly higher success rate in locating sample regions of interest, such as cell structures, than the prior art. This applies both in the case of the light-microscopy manual search/comparison of the two light-microscopy images and for an automatic correlation of the image data using an algorithm. Even if only small sample regions remain undamaged after detaching the sample holder, they can be clearly identified and thus optimally utilized. Even if the sample holder breaks in the steps prior to polymerization (e.g. during high-pressure freezing), (larger) fragments of the sample holder can be successfully assigned to the sample after polymerization and are thus not lost for planned examinations.

There are now various possibilities for embodying and developing the teaching of the present disclosure in an advantageous manner. For this purpose, reference is made to the claims subordinate to claim 1 and to the following explanation of the disclosure with reference to the drawings. In connection with the explanation of the preferred embodiments of the disclosure based on the drawings, preferred configurations and developments of the teaching in general are also explained.

The term "and/or" includes any combination of one or more of the associated listed elements and may be abbreviated to "/."

Although some aspects have been described in the context of a device, it is clear that these aspects also represent a description of the corresponding method, where a block or a device corresponds to a method step or a function of a method step. Similarly, aspects that are described as part of a method step also represent a description of a corresponding block or element or a property of a corresponding device.

DETAILED DESCRIPTION

In the drawings, components that are identical or structurally or functionally equivalent to one another are indicated with identical reference signs and, for the sake of clarity, are not explained again. Explanations regarding device features or corresponding components also relate to correspondingly performed method steps, and vice versa.

Figure 1A:
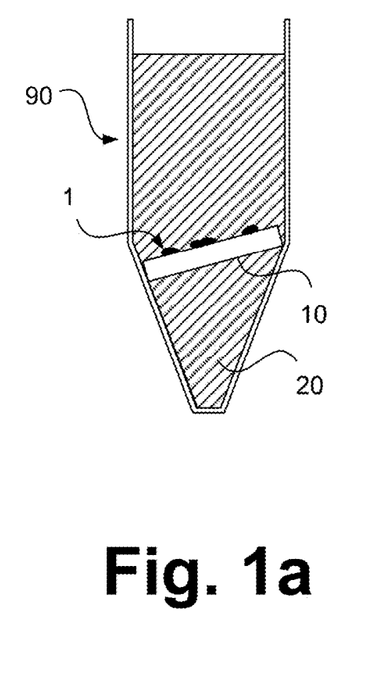
FIGS. 1*a* and 1*b* show variants of cryotubes.
Figure 1B:
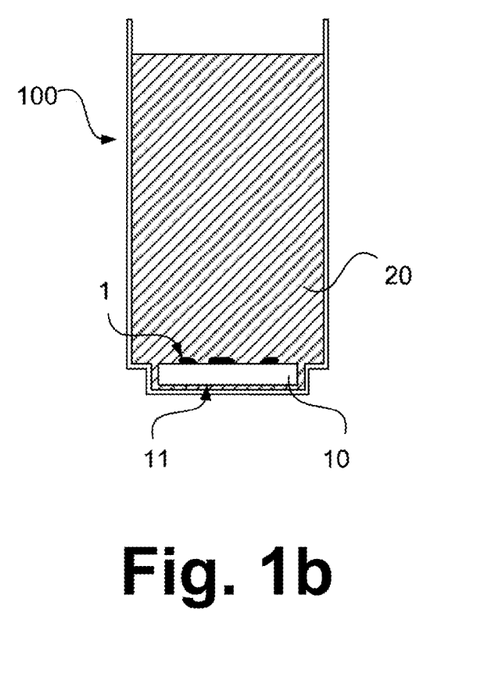

FIGS. 1*a* and 1*b* show variants of cryotubes in a greatly simplified and purely schematic representation. FIG. 1*a* shows a cryotube 90 with a conical base in detail. In this case, the sample holder, as shown in FIG. 1*a* and denoted by 10, is often not perpendicular to the longitudinal axis of the cryotube 90 and has polymerized solid synthetic resin blocks of an embedding medium 20 shown hatched on both sides, which cannot be easily detached. In this case, preparation support fragments are typically copolymerized and can usually only be freed with great effort. A sample arranged on the sample holder 10 is denoted by 1.

In a preferred variant of the method according to the disclosure, the preparations are cured or polymerized using flow-through rings/inserts or similarly constructed cryotubes with a planar and sufficiently large base. Such a type of cryotube (a flow-through insert) is shown in FIG. 1*b* and denoted by 100, with FIG. 1*b* only showing a flow-through ring purely schematically, but also optionally one of several chambers (portions) for a flow-through insert to receive a sample. These chambers have a diameter of 6 mm to accommodate a correspondingly large sample holder or sapphire. Such a flow-through insert may or may not have an outward border. In the latter case, it must be placed in a surrounding container such as a tray before the embedding medium 20 is added.

As can be seen in FIG. 1*b*, when such cryotubes are used, the sample holders 10 are positioned on a flat surface, and on the back 11 of the sample holder 10 there is only a very thin layer of the embedding medium 20, for example the synthetic resin. The flow-through ring used can consequently be easily detached from this synthetic resin layer and the thin synthetic resin layer can be mechanically removed relatively easily from the smooth carrier material, for example with a scalpel. This method can also be used for sample holder fragments (parts of a sample holder). In contrast to this, when the sample holder is positioned in a cryotube, as shown for example in FIG. 1*a*, it is often not perpendicular to the axis and has solid blocks of synthetic resin polymerized onto both sides, which cannot be easily detached. In this case, fragments of the sample holder 10 are typically copolymerized and can usually only be removed with great effort.

After releasing the synthetic resin block from the polymerization mold 90, 100 (i.e. a cryotube), the back of the small carrier plate or sample holder 10 must first be freed from the embedding medium 20, for example the synthetic resin. In the case of sapphire as the carrier material and, for example, epoxy resin as the synthetic resin, this removal can be very efficiently carried out mechanically with a scalpel. The use of suitable solvents is also possible.

When the back of the preparation or sample holder 10 has been thoroughly cleaned (it can also be subsequently washed with ethanol, for example), it is received in a holder and placed on the microscope table. It can now be examined under a light microscope, ideally using the same lens or even the same microscope (or a microscope of the same type), since the same carrier material is also being irradiated. This ensures that, for example, the magnification and resolution of the images are as identical as possible. However, a different lens can also be used, and the resulting effects must then be taken into account when evaluating the data, e.g. the different magnification.

Transmitted light microscopy can be used as a light-microscopy procedure. If the preliminary preparation has not destroyed the preparation fluorescence, the use of fluorescence microscopy is also conceivable. If the synthetic resin itself fluoresces (autofluorescence, such as in the case of epoxy resin), this fluorescent light can be used as a transmitted light source for the preparation.

The cured/polymerized preparation, together with carrier material, is now advantageously scanned in the same way, and is in any case scanned at the same points, as the living preparation. These scans are also combined to form complete images and can (when using the same lens) be brought into alignment with the living cell images substantially by rotation. If a different lens is used, the magnification of one of the two groups of images must also be adjusted. The examination and image capturing are advantageously carried out through the sample holder.

The images can now be made to coincide and a user can, for example, identify individual cells or cell groups through partially transparent superimposition and measure their position for further preparation from the images. However, this adjustment can just as easily be done automatically in a machine-based manner, with coordinates ideally being captured (semi-automatically or automatically) and stored at the same time.

Figure 2A:
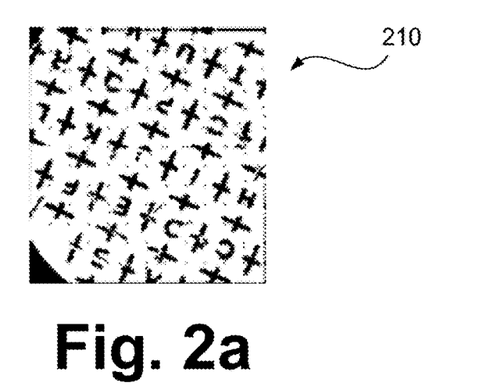
FIGS. 2*a* through 2*c* show various light-microscopy images which have been captured as part of a method according to embodiments of the disclosure.
Figure 2B:
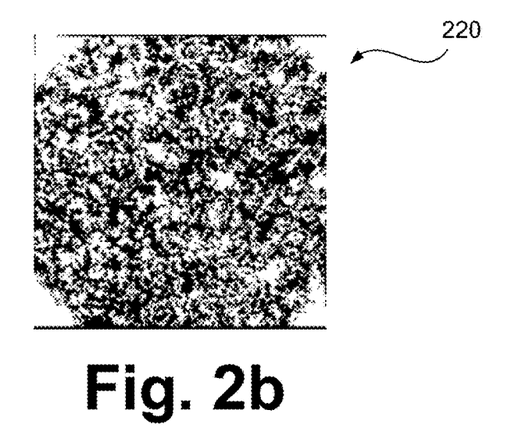
Figure 2C:
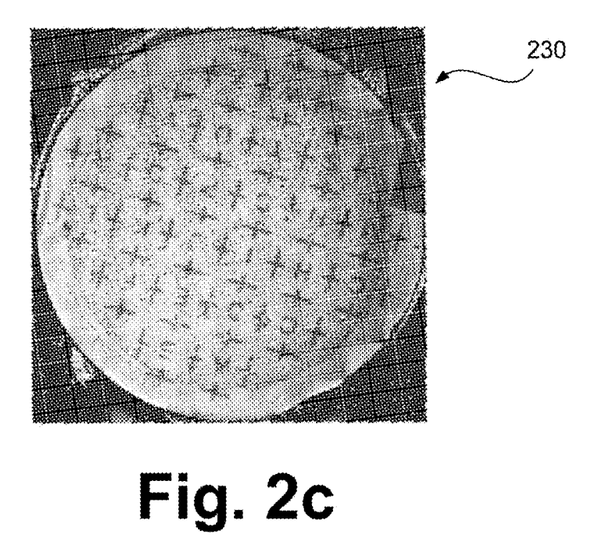

FIGS. 2a and 2b show composite images 210 and 220 of an examined living preparation in transmitted light imaging and fluorescence imaging. In the example shown, images 210 and 220 were obtained with a 40× lens. Image 210 was obtained using transmitted light microscopy. According to image 220, fluorescence markers attached to the preparation were excited with a wavelength of 470 nm and detected with a wavelength of 510 nm. These are examples of images from the first light-microscopy procedure. FIG. 2c shows a composite capture 230 (the second image) of the sample or the preparation block through the carrier sapphire (i.e. the sample holder). It is a transmitted-light bright-field image taken with a 20× lens. The mesh/lattice structure on the sample holder is clearly visible here and can be used for orientation.

Figure 3:
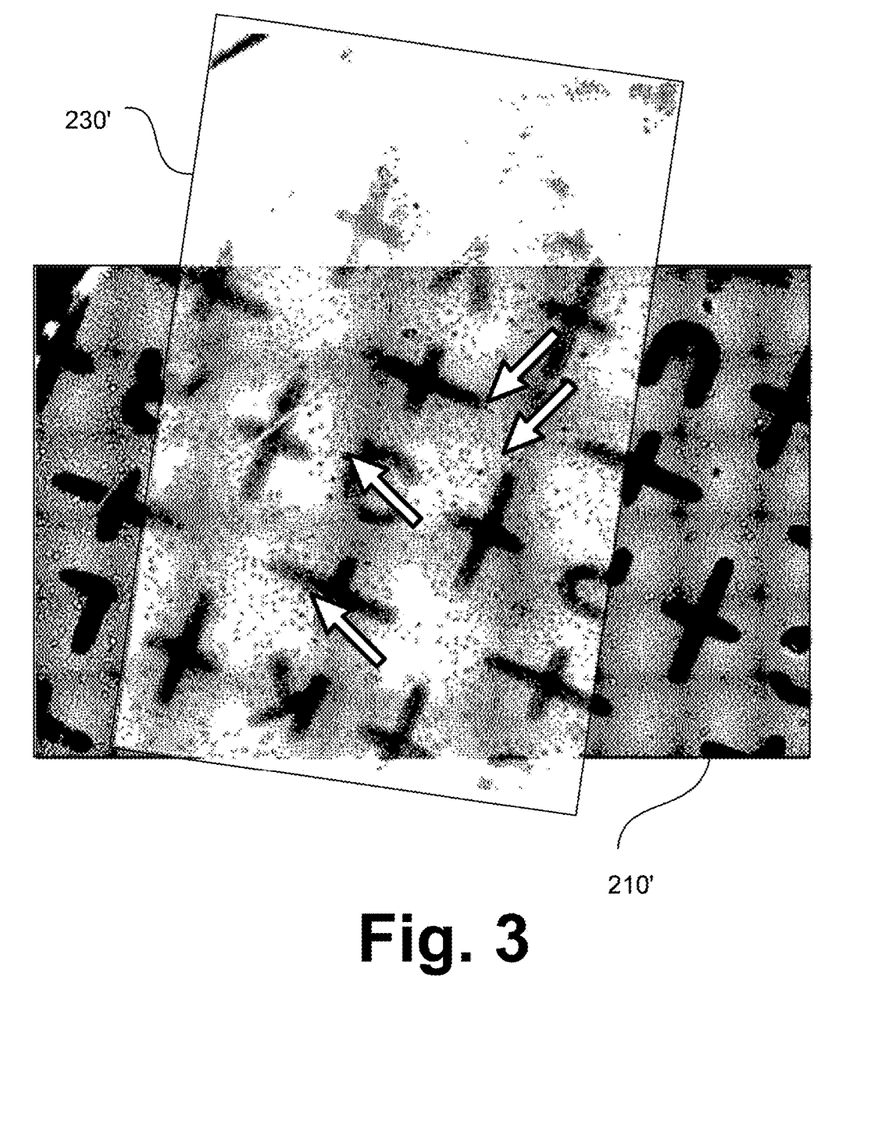
FIG. 3 shows a superimposition of two images that were captured as part of a method according to an embodiment of the disclosure.

As shown in FIG. 3, these images, labeled 210' and 230' here, can now be overlaid in a partially transparent manner, for example for evaluation by the user: for example, the arrows indicate correlated cell formations of interest.

Alternatively, such an identification of corresponding image portions can also be carried out using a software-based algorithm (correlation software): this correlation software evaluates the first and second image data and uses corresponding regions to determine a coordinate transformation between the first and second image. In this way, the coordinates of the sample regions that were originally of interest can be determined directly in the preparation block and made available for further process steps, which can be carried out manually or automatically. Such a correlation algorithm can also be based on machine/deep learning.

Figure 4:
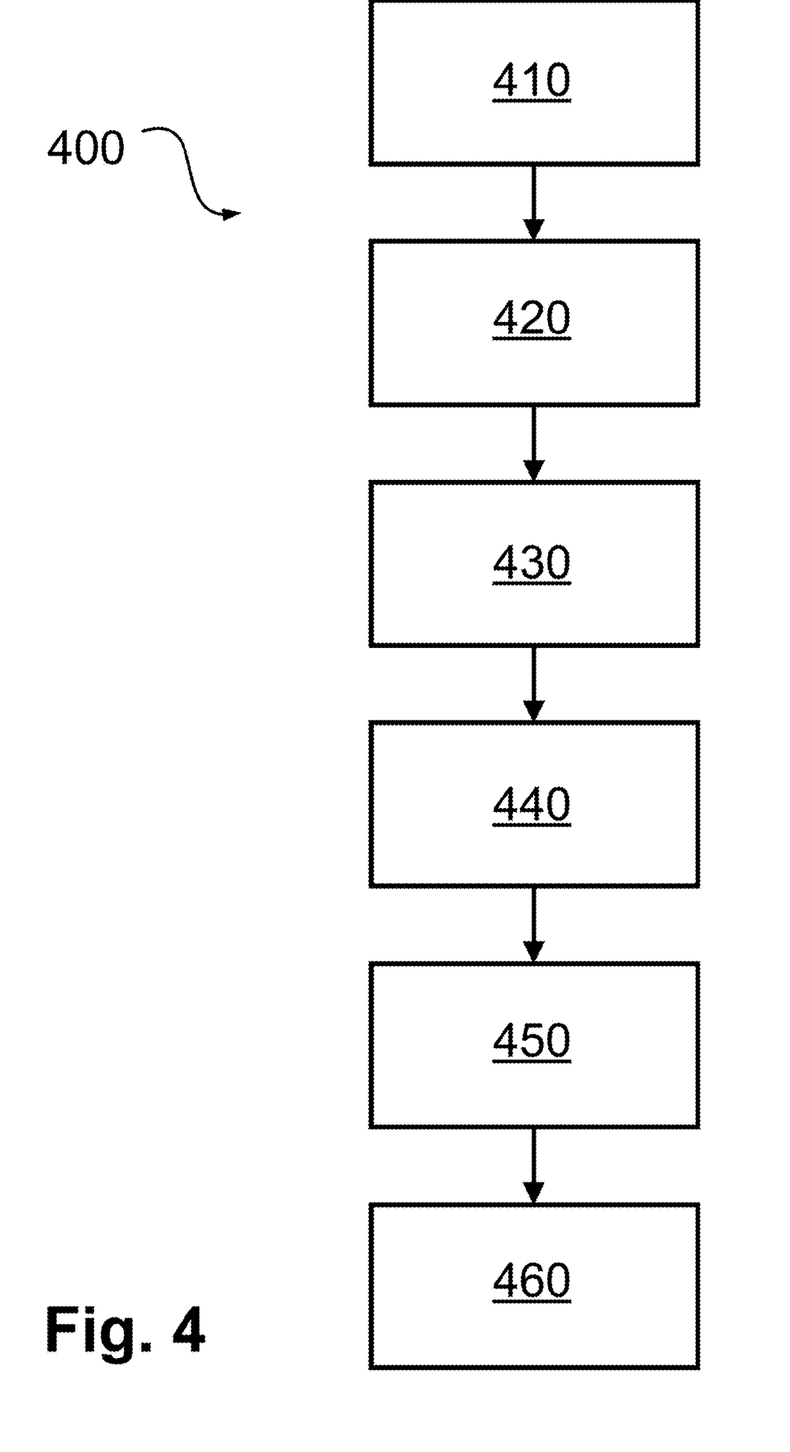
FIG. 4 shows a flowchart to clarify the method according to the disclosure.

Finally, FIG. 4 shows the individual method steps of a method 400 according to an embodiment of the disclosure as a progression diagram: In a first step 410, a biological sample is applied to, for example grown on, a preferably transparent sample holder. After the subsequent capturing of a first light-microscopy image, for example a transmitted light image or a fluorescence microscopic image of the sample, in step 420, in a further step 430, cryofixing, freeze-substitution and subsequent infiltration and embedding of the sample with an embedding medium, such as a synthetic resin, are carried out. This embedding medium is now cured in step 440. The preparation block and the sample holder are then removed from the embedding mold. Then (after an optional detachment or removal of the cured embedding medium from the back of the sample holder) further light-microscopy imaging of the sample is carried out in the subsequent step 450, in particular through the sample holder. The images from steps 420 and 450 are now compared with one another and corresponding image portions or sample regions are identified. This step can either be carried out by a user or automated, for example by machine/deep learning-supported image recognition methods. As a result, in the last step 460, a coordinate transformation between the two images or image data is determined. This can be used to clearly assign image regions from the second image to image regions from the first image after the sample holder has been separated from the preparation block, even if parts of the sample were destroyed as a result. In other words, the position of sample regions identified in the first image can also be easily determined in the second image and in the electron-microscopy image after the sample has been frozen and embedded.

Figure 5:
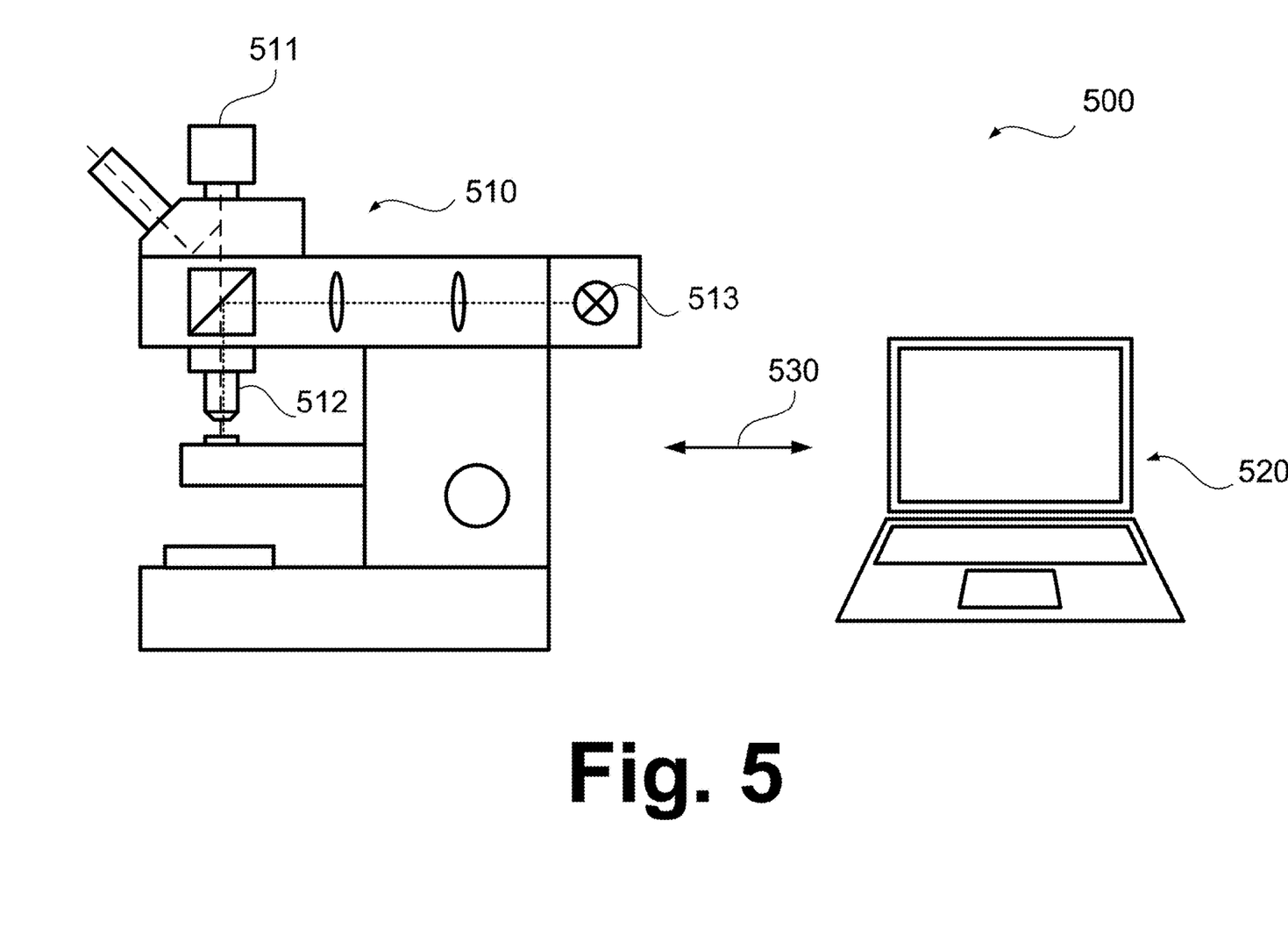
FIG. 5 shows a microscope system that can be used to carry out a method according to an embodiment of the disclosure.

FIG. 5 shows a microscope system 500 which can be designed to carry out a method according to an embodiment of the disclosure and which can have a (fluorescence) microscope 510 and a computer system 520, which can communicate with one another in a wired or wireless manner, as is illustrated by a double arrow 530. The microscope 510 can be upright (as shown), but alternatively can be an inverted microscope.

The computer system 520 can be configured to execute a machine learning algorithm. The computer system 520 and the microscope 510 can be separate units, but can also be integrated together in a common housing. The computer system 520 can be part of a central processing system of the microscope 510 and/or the computer system 520 can be part of a sub-component of the microscope 510, such as a sensor, an actuator, a camera unit 511, or an illumination unit, etc. of the microscope 510.

Some or all method steps suitable for this may be performed by (or using) a hardware device, such as a processor, microprocessor, programmable computer, or electronic circuit. In some embodiments, one or more of the main method steps can be performed by such a device.

In particular, the capture of a first image, previously designated 420, of a sample applied to a sample holder can be carried out using a first light-microscopy procedure using the camera unit 511 of the microscope 510, as can the capture of a second image, previously designated 450, of the sample embedded in the cured embedding medium using a second light-microscopy procedure. In particular, the capture 420 of the first image and the capture 450 of the second image can be carried out using the same microscope 510, in particular using the same lens 512 of the microscope 510 and/or the same magnification and/or the same scan region and/or the same image resolution.

The microscope 510 can be designed for reflected light illumination or transmitted light illumination and the method can in particular include an autofluorescence of the embedding medium being excited by the embedding medium being illuminated by an artificial light source 513, for example an LED or a laser, in order to capture a second image 230 according to the disclosure.

In particular, corresponding sample regions can be assigned on the basis of the first image data and the second image data using a first algorithm that is executed in the computer system 520. In particular, a first coordinate system can be assigned to a first image and a second coordinate system can be assigned to a second image, and, based on the image regions identified with one another, a coordinate transformation between the first coordinate system and the second coordinate system can be determined by the first or a second algorithm. The second coordinate system and the coordinate transformation can be used together with the image data of the second image for further evaluation and/or processing steps and can be temporarily stored in the computer system 520, for example.

Figure 6:
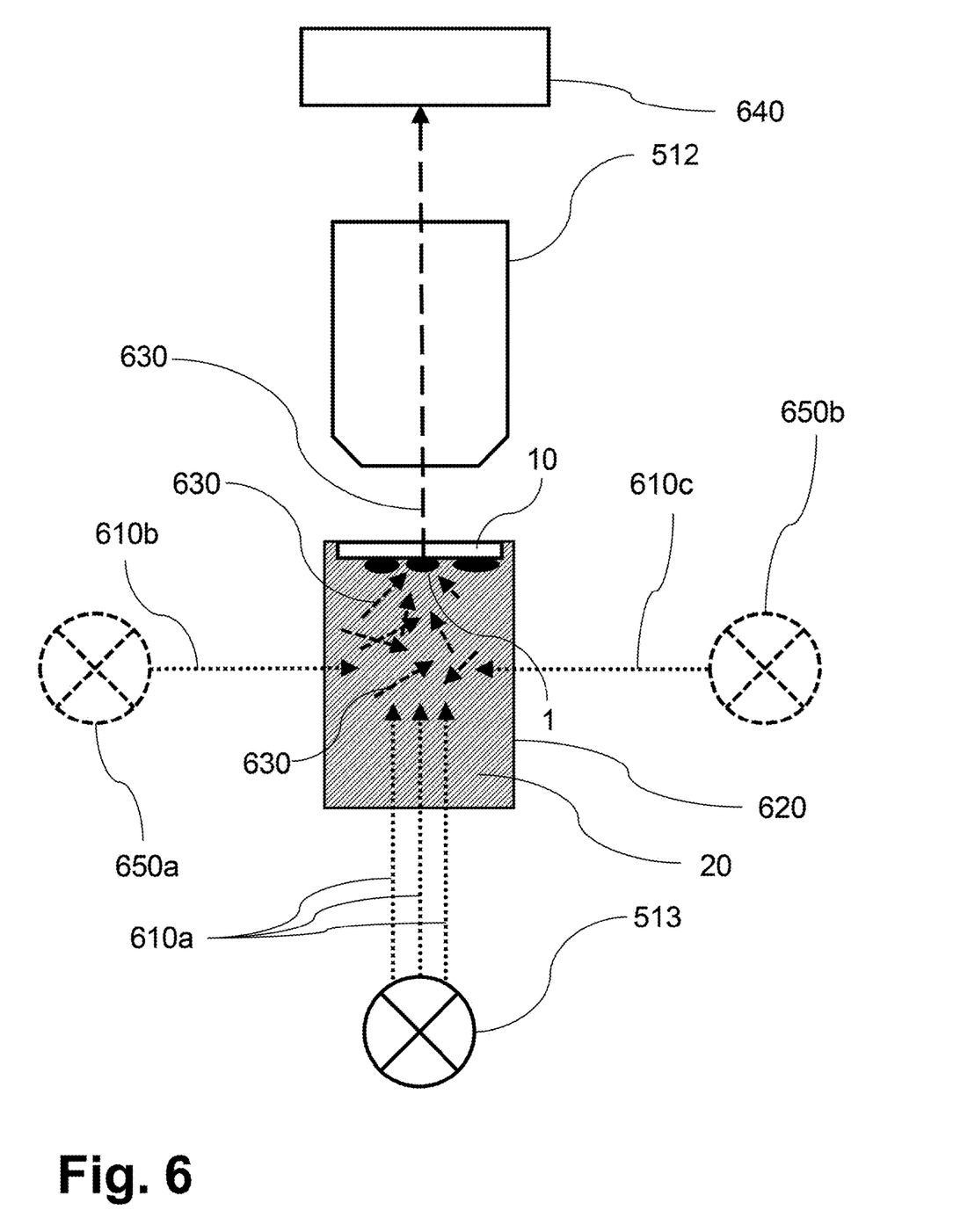
FIG. 6 shows several possibilities according to the disclosure for illuminating a preparation block for capturing an image.

FIG. 6 schematically shows a possibility according to the disclosure for illuminating a sample 1 in an embedding medium 20 and for capturing a second image 230: light 610a is radiated into the preparation block 620 with the sample 1 by means of an artificial light source 513, for example a laser or an LED. There are several options for illuminating the sample 1: the light 610a is either itself used for transmitted light illumination of the sample 1 and/or excites autofluorescence 630 in the embedding medium 20 (which is then used for transmitted light illumination of the sample 1) and/or excites fluorescence in the sample 1 (if the sample contains suitable fluorophores). The light 630 transmitted through the sample holder 10 is now captured by means of a lens 512 and guided to a detector 640, for example a camera or a point detector. The variants illustrated in FIG. 6 show detection through the sample holder 10, but this does not necessarily have to be the case; detection can also be carried out from other directions. FIG. 6 only shows a particularly advantageous embodiment of the disclosure. Likewise, the preparation block 20 does not necessarily have to be illuminated from the direction 610a shown (i.e. from the side of the preparation block 620 facing away from the sample holder 10 and the lens 512). Alternatively or additionally, illumination from other directions 610b, 610c is also conceivable, for which purpose the light source 513 can be placed accordingly or one or more additional light sources 650a, 650b can be used. The splitting and/or spreading of light from a light source 513 is also conceivable in order to enable light to be radiated onto the preparation block 20 from different directions and to ensure a particularly advantageous excitation of autofluorescence.

Figure 7:
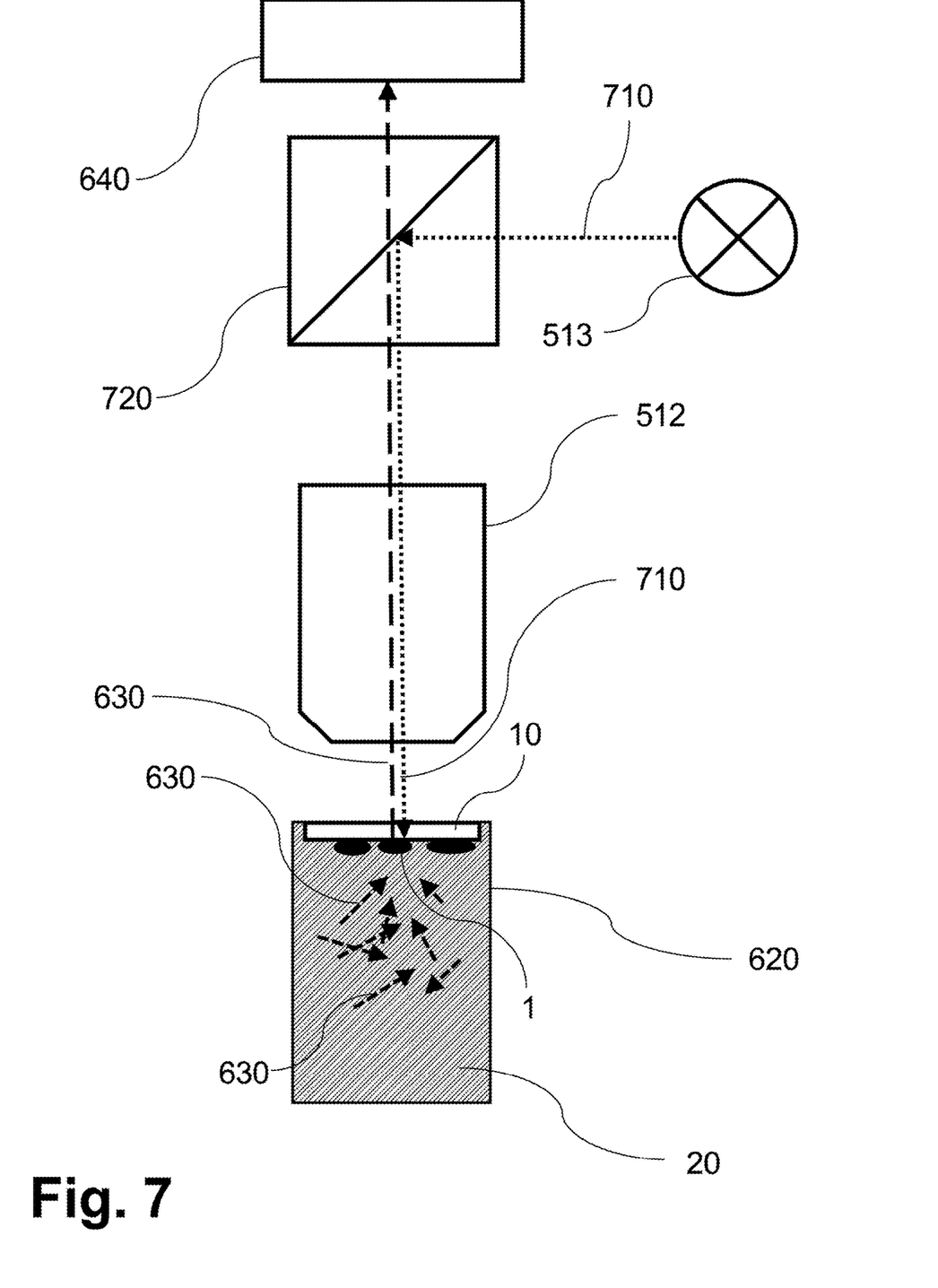
FIG. 7 shows a further possibility according to the disclosure for illuminating a preparation block for capturing an image.

It is particularly advantageous if the illumination is provided through the sample holder 10, with the artificial light source 513 serving to stimulate fluorescence in the sample 1 and/or autofluorescence in the embedding medium 20. This embodiment possibility is shown schematically in FIG. 7. Suitable guidance of the light 710, which serves to illuminate the sample or the embedding medium 20, and of the light 630 to be detected can be implemented by means of a beam splitter 720, which is preferably a dichroic beam splitter.

What is claimed is:

1. A method for the microscopic examination of a sample, the method comprising the following steps:
  a. applying the sample to a sample holder, wherein the sample holder comprises a transparent carrier material;
  b. capturing a first image of the sample applied to the sample holder using a first light-microscopy procedure, wherein the first image is represented by first image data;
  c. cryofixing, freeze-substituting, and subsequently infiltrating and embedding the sample together with the sample holder with an embedding medium in an embedding mold;
  d. curing the embedding medium;
  e. removing the sample embedded in the cured embedding medium from the embedding mold together with the embedding medium and the sample holder;
  f. capturing a second image of the sample embedded in the cured embedding medium using a second light-microscopy procedure,
  wherein the second image is represented by second image data and at least partially identical regions of the sample are captured by capturing the first image and capturing the second image; and
  g. identifying at least one portion of the first image and one portion of the second image which show identical regions of the sample.

2. The method according to claim 1, wherein the second image is captured through the sample holder.

3. The method according to claim 1, wherein the first image is captured using a microscope, and the second image is captured using the same microscope used to capture the first image.

4. The method according to claim 3, wherein the first image is captured using a lens of the microscope, a magnification of the microscope, a scan region of the microscope, and an image resolution of the microscope, and wherein the second image is captured using at least one of the lens used to capture the first image, the magnification used to capture the first image, the scan region used to capture the first image, and the image resolution used to capture the first image.

5. The method according to claim 1, wherein the transparent carrier material is a glass.

6. The method according to claim 1, wherein the transparent carrier material is a sapphire.

7. The method according to claim 1, wherein the sample is kept under controlled environmental conditions during the step of capturing the first image.

8. The method according claim 1, wherein a portion of the embedding medium on a side of the sample holder facing away from the sample is removed from the side of the sample holder facing away from the sample before the step of capturing the second image.

9. The method according to claim 8, wherein the embedding medium on the side of the sample holder facing away from the sample is removed mechanically.

10. The method according to claim 1, wherein the second light-microscopy procedure is a transmitted-light brightfield microscopy procedure.

11. The method according to claim 1, wherein the embedding medium has an autofluorescence and the second light-microscopy procedure uses the autofluorescence to illuminate the sample.

12. The method according to claim 1, wherein the infiltrating and embedding of the sample with the embedding medium comprises the following steps:
  a. placing the sample holder with the sample in a cryotube having a flat base, wherein a maximum extension of the base is greater than or equal to a maximum extension of the sample holder; and
  b. feeding the embedding medium into the cryotube with the sample at least until the sample is completely surrounded by the embedding medium, wherein the sample holder is oriented so as to be parallel or substantially parallel to the flat base of the cryotube even after the feeding of the embedding medium.

13. The method according to claim 1, wherein corresponding portions of the first image and the second image which show identical regions of the sample are identified on the basis of the first image data and the second image data by a first algorithm and/or manually.

14. The method according to claim 13, wherein a first coordinate system is assigned to the first image and a second coordinate system is assigned to the second image and, based on the corresponding portions of the first image and the second image which show identical regions of the sample, a coordinate transformation between the first coordinate system and the second coordinate system is determined by the first algorithm or by a second algorithm.

15. The method according to claim 14, wherein the coordinate transformation is determined in portions, such that different coordinate transformations are defined for different sample regions and/or different cell types within the sample.

16. The method according to claim 14, wherein the second coordinate system and the coordinate transformation are used together with the second image data for further evaluation and/or processing steps.

17. The method according to claim 1, wherein the method further comprises the following steps:
   h. at least partially detaching the cured embedding medium together with the cured sample from the sample holder;
   i. preparing a sample portion by cutting the sample in the embedding medium embedding the sample; and
   j. examining the sample portion in an electron microscope.

18. The method according to claim 17, wherein the cutting of the sample is performed using a microtome.

\* \* \* \* \*